(12) United States Patent
Titball et al.

(10) Patent No.: US 7,524,507 B1
(45) Date of Patent: Apr. 28, 2009

(54) RECOMBINANT MICROORGANISMS

(75) Inventors: Richard William Titball, Salisbury (GB); Helen Lisa Bullifent, Salisbury (GB)

(73) Assignee: The Secretary of State for Defense in Her Brittanic Majesty's Government of the United Kingdom of Great Britain and Northern Ireland (GB)

( * ) Notice: Subject to any disclaimer, the term of this patent is extended or adjusted under 35 U.S.C. 154(b) by 244 days.

(21) Appl. No.: 10/070,882

(22) PCT Filed: Sep. 6, 2000

(86) PCT No.: PCT/GB00/03402

§ 371 (c)(1),
(2), (4) Date: Mar. 11, 2002

(87) PCT Pub. No.: WO01/19974

PCT Pub. Date: Mar. 22, 2001

(30) Foreign Application Priority Data

Sep. 10, 1999 (GB) .................................. 9921275.5
Jul. 12, 2000 (GB) .................................. 0017000.1

(51) Int. Cl.
*A61K 39/02* (2006.01)
*A01N 63/00* (2006.01)
*C12N 15/00* (2006.01)
*C12N 15/09* (2006.01)
*C12P 21/06* (2006.01)
*C12P 21/04* (2006.01)

(52) U.S. Cl. ................ 424/200.1; 424/234.1; 424/93.4; 424/93.48; 424/93.2; 435/320.1; 435/69.3; 435/71.1; 435/69.1

(58) Field of Classification Search .............. 435/320.1, 435/69.3, 69.1, 71.1; 424/200.1, 93.2, 93.4, 424/234.1, 93.48, 258.1
See application file for complete search history.

(56) References Cited

U.S. PATENT DOCUMENTS 5,985,285 A * 11/1999 Titball et al. ............. 424/234.1

FOREIGN PATENT DOCUMENTS

WO    WO 95/18231    *   7/1995
WO    WO 96/28551        9/1996

OTHER PUBLICATIONS

Bowie et al. Science 247: 1306-1310, 1990.*
Lazar et al. Mol. Cellular Biol. 8: 1247-1252, 1988.*
Burgess et al. J. Cell Biol. 111:2129-2138, 1990.*
Leary et al. Microb. Pathogen. 23: 167-179, 1997.*
Glynn et al. Vaccine 23: 1957-1965, 2005.*
Leary et al. Contrib. Microbiol. Immunol. 13: 216-217, 1995.*
R. Titball, et al., "Expression of the *Yersinia pestis* Capsular Antigen (F1 Antigen) on the Surface of an aroA Mutant of *Salmonella typhimurium* Induces High Levels of Protection against Plague," Infection and Immunity, May 1997, pp. 1926-1930.
E. Hohmann, et al., "Macrophage-inducible expression of a model antigen in *Salmonella typhimurium* enhances immunogenicity," Proc. Natl. Acad. Sci. USA Microbiology, Mar. 1995, vol. 92, pp. 2904-2908.
M. Roberts, et al., "Oral Vaccination against Tetanus: Comparison of the Immunogenicities of *Salmonella* Strains Expressing Fragment C from the nirB and htrA Promoters," Infection and Immunity, Jul. 1998, pp. 3080-3087.
S. McSorley, et al., "Vaccine Efficacy of *Salmonella* Strains Expressing Glycoprotein 63 with Different Promotors," Infection and Immunity, Jan. 1997, pp. 171-178.
H. Bullifent, et al., "Antibody responses to *Yersinia pestis* F1-antigen expressed in *Salmonella typhimurium* aroA from in vivo-inducible promoters," Vaccine, 2000 vol. 18, pp. 2668-2676.

* cited by examiner

*Primary Examiner*—S. Devi
(74) *Attorney, Agent, or Firm*—Kilpatrick Stockton LLP (57) ABSTRACT

A method of enhancing expression of a desired protein at mucosal effector sites, the method including placing the protein to be expressed under the control of a promoter having SEQ ID NO: 2, SEQ ID NO: 3 or SEQ ID NO: 4, or a fragment or variant of any of these that has promoter activity, and causing expression in mucosal cells. Constructs used in the methods, as well as suitable recombinant gut-colonising microorganisms such as a *Salmonella* spp., are also described. Such organisms are useful in the preparation of vaccines.

10 Claims, 9 Drawing Sheets

$P_{lac}$   5'
CGCCCAATACGCAAACCGCCTCTCCCCGCGCGTTGGCCGATTCATTAATGCAGCTGGCACGACAGGTTTCC
CGACTGGAAAGCGGGCAGTGAGCGCAACGCAATTAATGTGAGTTAGCTCACTCATTAGGCACCCCAGGCTT
TACACTTTATGCTTCCGGCTCGTATGTTGTGTGGAATTGTGAGCGGATAACAAT 3'
(SEQ ID NO 1)

$P_{phoP}$   5'
GTGACTCTGGTCGACGAACTTAAATAATGCCTGCCTCACCCTCTTTTCTTCAGAAAGAGGGTGACTATTTG
TCTGGTTTATTAACTGTTTATCCCCAAAGCACCATAATCAACGCTAGACTGTTCTTATTGTTAACACA 3'
(SEQ ID NO 2)

$P_{pagC}$   5'
GTTAACCACTCTTAATAATAATGGGTTTTTATAGCGAAATAGACTTTTTTATCGCGTGTTCAATATTTGCGT
TAGTTATTATTTTTTTGGAATGTAAATTCTCTCTAAACACAGGTGATATTTATGTTGGAATTGTGGTGTTG
ATTCTATTCTTATAATATAACAAGAAATGTTGTAACTGATAGATATATTAAAAGATTAAATCGGAGCGGGA
ATAAAGCGTGCTAAGCATCATCGTGAATATGATTACAGCGCCTGCGATGGCATATAACCGTATTGCGGATG
GAGCGTCACGTGAGGACTGTGAAGCACAATGCGATATGTTCTGATTATATGGCGAGTTTGCTTAATGACAT
GTTTTTAGCCGAACGGTGTCAAGTTTCTTAATGTGGTTGTGAGATTTTCTCTTTAAATATCAAAATGTTGC
ATGGGTGATTTGTTGTTCTATAGTGGCTAAACACTTTATGGTTTCTGTTAAATATATATGCGTGAGAAAAA
TTAGCATTCAAATCTATAAAAGTTAGATGACATTGTAGAACCGGTTACCTAAATGAGCGATAGAGTGCTTC
GGTAGTAAAAATATCTTTCAGGAAGTAAACACATCAGGAGCGATAGCGGTGAATTATTCGTGGTTTTGTCG
ATTCGGCATAGTGGCGATAACTGAATGCCGGATCGGTACTGCAGGTGTTTAAACACACCGTAAATAATAAG
TAGTA 3'
(SEQ ID NO 3)

$P_{ompC}$   5'
TAAACAGACATTCAGAAGTGAATGACGGTAATAAATAAAGTTAATGATGATAGCGGTCACTATTTTAGTTG
CGAATGAAGATTCTGTTTTATCATTCAGTGCTATGAATTTCATCAATTTAACCCGTTGATTTTAAAAGTTT
CGTGAAATATATTTTGTCTATTTGTGCTTATTTTTACTTGATTTTTGCTTTAAAAAAGTTCCGTAAAATTC
ATATTTTGAAACATCTATATAGATAACTGTAACATCTTAAAAGTTTTAGTATCATATTCGTGTTGGATTAT
TCTGTATTTTTGCGGAGAATGGACTTGCCGACTGGTTAATGAGGGTTAACCAGTAAGCAGTGGCATAAAAA
AGCAATAAAGGCATAT 3'
(SEQ ID NO 4)

The locations of oligonucleotide primers used in the PCR are shown underlined. Promoter regions are shown in bold and repeated sequences upstream of these promoters are shown double underlined

Fig.7b.

RECOMBINANT MICROORGANISMS

CROSS REFERENCE TO RELATED APPLICATIONS

This application claims priority to Great Britain Application No. 9921275.5 filed on Sep. 10, 1999 and Great Britain Application No. 0017000.1 filed on Jul. 12, 2000 and International Application No. PCT/GB00/03402 filed on Sep. 6, 2000 and published in English as International Publication Number WO 01/19974 A3 on Mar. 22, 2001, the entire contents of which are hereby incorporated by reference.

This application is a 35 U.S.C. §371 of PCT/GB96/00571, filed Mar. 13, 1996.

BACKGROUND OF THE INVENTION

The present invention relates to recombinant microorganisms, in particular gut-colonising organisms, which are useful for example in the delivery of antigenic material and thus form the basis of vaccines. Vaccines comprising these organisms and promoter sequences for use in them form a further aspect of the invention.

Attenuated mutants of *Salmonella typhi* (e.g. aroA, aroC, htrA) are currently being evaluated as live, oral vaccines against typhoid fever (Tacket C O, et al., Infect. Immun. 1997;65:452-6). These mutants have also attracted attention as carriers for guest (vaccine) antigens but suitable animal models for testing these vaccines are not available. In view of this, many workers have used *Salmonella typhimurium* aroA expressing guest antigens for investigating the immune responses induced after oral vaccination of mice.

The unregulated expression of foreign genes within *Salmonella* species such as *S. typhimurium* can lead to plasmid instability, yet the stable expression of the guest antigen at the appropriate site in the body is necessary for the induction of a protective response. One approach to promote the stable expression of guest antigens involves the chromosomal integration of the heterologous gene. However, this may reduce the immune response because of gene dosage effects (Covone M G, et al., Infect. Immun. 1998;66:224-31).

The balanced lethal system (Curtiss R III, et al., Res. Microbiol. 1990;141:797-805, Nakayama K, et al., Bio/Technology 1988;6:693-97) relies on the complementation of a lethal mutation by a plasmid which also encodes the guest antigen. Whilst this ensures retention of the plasmid, the gene encoding the guest antigen itself may be deleted. An alternative approach involves the use of promoters which are induced within host tissues to direct guest antigen expression at that site. Because the gene is only expressed after certain environmental cues have been recognised, this approach might reduce the selective pressure towards deleting the gene.

This solution to the problem of expression of guest antigens has also been identified by other workers. A variety of antigens have been expressed in *S. typhimurium* from the nirB promoter which is upregulated under anaerobic conditions and within host cells (Oxer M D, et al. Nucleic Acids Res. 1991;19:2889-92). Guest antigens delivered using the nirB promoter system induce superior responses than the same antigens delivered from a constitutive promoter. In addition, the nirB promoter-driven genes were maintained more effectively in the *Salmonella* host strain. More recently, it has been shown that the htrA and osmC promoter can be used to direct expression of guest antigens in *Salmonella* (McSorley S J, et al., Infect. Immun. 1997;65:171-78, Roberts M, et al., Infect. Immun. 1998;66:3080-87). However, it is likely that these promoters will not be suited to the expression of all guest antigens.

Immunisation with the F1-antigen of *Y. pestis* has previously been shown to induce an antibody-mediated protective response against plague (Green M, et al., FEMS Microbiology and Immunology, 1998;23:107-13) and we have previously shown that the F1-antigen can be expressed in *S. typhimurium* (Oyston P C F, et al., Infect. Immun. 1995;63:563-68, Titball R W, et al., Infect. Immum. 1997;65:1926-30). The antigenic properties of F1-antigen have been exploited to investigate the ways in which different promoters, which are induced at different sites in the body, can be used to induce different antibody responses to guest antigens expressed in *S. typhimurium*. It is known that the invasion and spread of *S. typhimurium* within the host is accompanied by the expression of different subsets of genes which are involved in processes such as attachment and invasion, penetration of the epithelium and the infection of deep lymphoid tissue.

The OmpR/EnvZ two component regulatory system responds to changes in the osmotic strength and pH within *S. typhimurium* (Foster J W, et al., Microbiology 1994;140:341-52). It has been suggested that this system might play a role in allowing the bacterium to survive in the gut by regulating the expression of outer membrane porins such as OmpC (Pratt L A, et al., American Society of Microbiology, ASM Press, Washington D.C., 1995, pp105-27, Nikaido H, et al., Cellular and Molecular Biology. American Society for Microbiology, Washington D.C. 1987, p7-22, Garcia Véscovi E. et al., Cell. 1996;84:165-74).

The PhoP/PhoQ two-component regulatory system controls virulence properties such as survival within macrophages, resistance to host defence antimicrobial peptides and acid pH, invasion of epithelial cells, the formation of spacious vacuoles and the processing and presentation of antigens by activated macrophages (Miller S I. et al., Proc. Natl. Acad, Sci USA 1989;86:5054-58, Fields P I, et al., Science 1989;243: 1059-62, Pegues D A, et al., Mol. Microbiol. 1995;17:169-81, Wick M J, et al., Mol. Microbiol. 1995;16:465-76), in response to environmental magnesium concentration (García Véscovi E. et al., Cell. 1996;84:165-74). Over forty genes are regulated by this system in *S. typhimurium* (Soncini F C, et al., J. Bacteriol. 1996;178:5092-99) including the phoP gene, which is autoregulated (Soncini F C, et al., J. Bacteriol. 1995; 177:4364-71) and the pagC gene which encodes an envelope protein required for survival in the macrophage (Alpuche-Aranda C M, et al., Proc. Natl. Acad. Sci. USA 1992;89: 10079-83).

Attenuation of *Salmonella* by partial deletion of the pagC gene and fusion to a heterologous protein is described in U.S. Pat. No. 5,733,760.

The applicants have however found that certain promoters can be used advantageously in such systems to drive high levels of expression of heterologous proteins, in particular in mucosal cells.

OBJECTS OF THE INVENTION

Thus, the present invention provides a method of enhancing expression of a desired protein at mucosal effectors sites, the method comprising placing a nucleic acid encoding the protein to be expressed under the control of a promoter having SEQ ID NO 2, SEQ ID NO 3 or SEQ ID NO 4 or a fragment or variant or any of these which has promoter activity, and causing expression in mucosal cells.

Thus, the present invention provides a method of enhancing expression of a nucleic acid encoding a desired protein at mucosal effectors sites, said method comprising placing the protein to be expressed under the control of a promoter having SEQ ID NO 2, SEQ ID NO 3 or SEQ ID NO 4 or a fragment or variant or any of these which has promoter activity, and causing expression in mucosal cells.

In a particular embodiment, the invention uses a construct comprising a promoter selected from the $P_{ompC}$, $P_{phoP}$ and $P_{pagC}$ or fragment and variants thereof which can act as promoters, operatively interconnected with a nucleic acid which encodes a protein, able to induce a protective immune response against an organism, in a mammal to which it is administered, wherein said construct contains no further elements of the $_{ompC}$, $_{phoP}$ or $_{pagC}$ gene.

The present invention further includes a recombinant gut-colonizing microorganism which comprises a promoter selected from the $P_{ompC}$, $P_{phoP}$ and $P_{pagC}$ or fragments or variants thereof which can act as promoters, said promoter being operatively interconnected with a nucleic acid which encodes a heterologous protein, able to induce a protective immune response against a different organism, in a mammal to which it is administered.

In particular, the microorganism has been transformed with the construct described above.

DETAILED DESCRIPTION OF THE INVENTION

The term "heterologous protein" refers to proteins which are not native to the microorganism strain.

The three promoters ($P_{phoP}$, $P_{pagC}$ and $P_{ompC}$,) which are included in the organisms of the invention are induced at different stages in the infection process, and hence at different sites in the body. This approach allows the induction of different immune responses which provide protection against pathogens which colonise different host cell compartments. The sequence of these promoters has been elucidated previously, and these are given hereinafter in FIG. 6 as SEQ ID NOS 2, 3 and 4 respectively.

Their expression has been compared to that of the constitutively expressed lacZ gene promoter. As a result, recombinant gut-colonising microorganisms wherein antigen expression is driven by $P_{phoP}$ promoter forms a preferred embodiment of the invention.

The development of effective vaccines against pathogens is dependent not only on the identification of the appropriate protective antigens but also on the induction of an immune response at the site in the body which provides maximum protection against disease. For some pathogens, serum antibody provides protection against disease. However, many pathogens enter the body at a mucosal surface and protection against these diseases might therefore be dependent on the induction of mucosal immune responses. The *Salmonella* vaccine vector system is ideally suited to the delivery of many vaccine antigens since the vaccine delivery mechanism accurately mimics the natural disease, entering the body via the gut.

Thus in particular embodiment, the recombinant gut-colonising microorganism comprises a *Salmonella* spp. such as *Salmonella typhimurium* or *Salmonella typhi.*

The recombinant *Salmonella* evaluated here showed significant differences in their abilities to induce mucosal IgA antibody responses. Serum IgA levels were not a good predictor of mucosal IgA levels, in accordance with the general findings by other workers that these responses are not well correlated [Lu F X et al., Infect. Immun. 1999;67:6321-8; Russell M W et al., Infect. Immun. 1991;59:4061-70; and Wenneras C et al., Infect. Immun. 1999;67:6231-41]. After oral dosing all of the recombinant *Salmonella* would have entered the body via M-cells, and, if sufficient antigen was subsequently presented to immune effector cells then mucosal antibody responses would be expected. The finding that mucosal antibody in the gut was induced only after immunisation with recombinant *Salmonella* expressing F1-antigen from the phoP or pagC gene promoters suggests that these promoters directed high-level expression of F1-antigen within GALT. Peyer's patch cells taken from mice immunised with SL3261/p$P_{pagC}$-F1 or SL3261/p$P_{pnoP}$-F1 produced the highest levels of IgA supporting this suggestion.

Immunisation with *Salmonella* containing p$P_{phoP}$-F1 also resulted in detectable IgA antibody in the lungs. This is in accordance with the finding that this recombinant also induced the highest levels of IgA in the gut and might indicate that the SL3261/p$P_{phoP}$-F1 was more effective than SL3261/p$P_{pagC}$-F1 in inducing long-term expression of IgA.

Recombinant gut-colonising microorganisms of the invention are suitably attenuated so that the host does not experience significant harmful effects as a result of infection by the microorganism. Examples of attenuated mutants include aro mutants such as aroA and aroC mutants, apartate β-semialdehyde dehydrogenase (ASD) mutants, purine biosynthesis mutants, branched chain amino acid biosynthesis mutants, galactose epimerase (galE) mutants, regulatory mutants such as phoP and phoQ mutants, htrA serine protease mutants and adenyl cyclase mutants. Particular attenuated strains of *Salmonella,* such as *Salmonella typhi* include aroA, aroC and htrA mutants or triple mutants including all three mutations.

Recombinant gut-colonising microorganism as described above can be used to deliver a variety of antigenic agents, which can be used to induce a protective immune response against a wide range of pathogens. Pathogens, which may be targeted in this way, are those of humans or animals and include those listed in the Health and Safety Executive: "Categorisation of Biological Agents according to Hazard and Category of Containment", HMSO, ISBN 0717610381. Particular examples of antigenic agents, which may be included in the recombinant organisms of the invention, include those protective against tetanus such as tetanus toxin $H_c$ fragment, those protective against *Bacillus anthracis* such as *Bacillus anthracis* protective antigen (PA), those protective against *Bordetella pertussis* such as *Bordetella pertussis* P69 antigen, those protective against *Schistosoma mansoni* such as *Schistosoma mansoni* glutathione-S-transferase, those protective against cholera such as Fibrio cholera β sub-unit, those protective against Herpes simplex virus (HSV) such as HSV glycoprotein D, those protective against HIV infection such as HIV envelope protein, and those protective against *Escherichia coli* such as *E. coli* LTB submit or *E. coli* K88 antigen. Other suitable antigenic agents include those protective against *Mycobacterium tuberculosis* as well as agents that protect or enhance anti-tumour immunity. In particular, it has been found that where the heterologous protein is able to induce a protective immune response against *Yersinia pestis,* useful protective immunity is found. Examples of antigens, which can produce such a response, include the F1-antigen of *Yersinia pestis* or an antigenic fragment or variant thereof, or the V-antigen or *Yersinia pestis* or combinations thereof as described in WO 96/28551.

The expression "variant" refers to sequences of amino acids which differ from the base sequence from which they are derived in that one or more amino acids within the sequence are substituted for other amino acids. Amino acid substitutions may be regarded as "conservative" where an amino acid is replaced with a different amino acid with broadly similar properties. Non-conservative substitutions are where amino acids are replaced with amino acids of a different type. Broadly speaking, fewer non-conservative substitutions will be possible without altering the biological activity of the polypeptide. Suitably variants will be at least 60% homologous, preferably at least 75% homologous, and more preferably at least 90% homologous to the base sequence. Homology in this instance can be determined using in particular the Needleman-Wunsch algorithm with gap penalty of 8 using a standard PAM scoring matrix (Needleman S. B. and Wunsch C. D., J. Mol Biol. 1970, vol 48, 443-453).

The recombinant gut-colonising microorganisms described above are thus particularly suitable for use in the preparation of vaccines for therapeutic or prophylactic purposes, where they may be combined with a pharmaceutically acceptable carrier or diluent, as would be understood in the art.

In particular, the vaccines will be formulated so that they are adapted for oral administration and that the microorganism remains viable throughout any storage period. Thus they may preferably be in a form liquid form such as aqueous or oily suspensions, emulsions, syrups or elixirs.

The size of the dose for therapeutic or prophylactic purposes of will vary according to a wide variety of factors including the nature of the protective immune response sought, the nature of the antigen being employed, the severity of the conditions, the dosage regime in terms of primary and secondary boosting, the age and sex of the animal or patient and the gut-colonising ability of the particular microorganism used. In general however, a dosage of microorganism in the range of from $10^6$ to $10^9$ cfu will be administered as a single dosage.

Vaccine compositions may further comprise a buffer such as a bicarbonate buffer, in order to neutralise stomach acid.

Thus in a further aspect, the invention provides a method of inducing a protective immune response against a pathogen in a mammal, said method comprising administering to said mammal a recombinant gut-colonising microorganism which comprises a promoter selected from the $P_{ompC}$, $P_{phoP}$ and $P_{pagC}$ or fragments or variants thereof which can act as promoters, said promoter being operatively interconnected with a nucleic acid which encodes an antigen protein, able to induce a protective immune response against said pathogen, in a mammal to which it is administered.

In yet a further aspect, the invention provides the use of a promoter selected from $P_{ompC}$, $P_{phoP}$ and $P_{pagC}$ in the production of a vaccine comprising a recombinant gut-colonising organism.

The promoters used in this study are induced at specific sites in the body. They are preferably cloned into the microorganism in a low copy number vector, because high copy number plasmids have been shown to be unstable in *S typhimurium* (Coulson N M, et al., Microb Pathog. 1994;16:305-11).

The PhoP gene would be expected to be expressed at a basal level from the PhoPp2 promoter and upregulated in the phagosome of host cells as a result of activation of the PhoPp1 promoter (Soncini F C, et al., J. Bacteriol. 1995;177:4364-71). The PhoP/PhoQ regulatory system has been shown to regulate the expression of a variety of genes including pagC, and to be important for survival in macrophages (Miller S I. et al., Proc. Natl. Acad, Sci USA 1989;86:5054-58, Wick M J, et al., Mol. Microbiol. 1995;16:465-76).

Genes regulated by the PhoP/PhoQ system are also important for the virulence of orally delivered bacteria (Galan J E, et al., Microb Pathog. 1989;6:433-43). Expression of the ompC is gene is upregulated under conditions of high osmotic strength (Foster J W, et al., Microbiology 1994;140:341-52, Nikaido H, et al., Cellular and Molecular Biology, American Society for Microbiology, Washington D.C. 1987, pp7-22), such as those found within the gut, under control of the OmpR/EnvZ regulatory system (Pratt L A, et al., American Society for Microbiology, ASM Press, Washington D.C., 1995, pp105-27).

Whilst the different plasmids in *S. typhimurium* SL3261 were stable in vitro, there were marked differences in the stability of the plasmids in bacteria which had been delivered to mice by the oral route. Bacteria expressing the F1-antigen from the PagC promoter showed a much reduced ability to colonise mesenteric lymph nodes and appeared incapable of further invasion of the host. It is possible that the additional copies of the pagC promoter and upstream regulatory regions titrated out the available PhoP activator within the cell, and that this prevented the bacterium from responding to the environmental changes encountered after uptake by M-cells. However, recombinant *Salmonella* containing the $P_{phoP}$-F1 plasmid did not show a similar inability to invade the host.

This finding might be in accordance with the suggestion that phoP expression is only partially autoregulated by the phoP gene product (Fields P I, et al., Science 1989;243:1059-62). Additionally, it is possible that the high level of expression of F1-antigen from the pagC promoter in vivo placed a lethal metabolic load on the host bacterium.

These promoters are regulated by a variety of environmental stimuli in a manner which is not fully defined. Therefore, it is difficult to make meaningful comparisons of the strengths of these promoters in vitro. Thus, in vivo testing of these promoters to identify those most suitable for use for the expression of guest antigens has been carried out.

All of the recombinant *Salmonella* induced similar levels of antibody against the whole bacterium. This finding was unexpected for bacteria containing $pP_{pagC}$-F1, since these bacteria were unable to invade deep host tissues and were recovered only at low levels from mesenteric lymph nodes. This recombinant *Salmonella* also induced IgG and IgA antibody against the F1-antigen. This suggests that the initial interaction of the bacteria with M-cells is critical in determining the immune response to the bacterium and to guest antigens. This conclusion is supported by the finding that *Salmonella* containing $pP_{pag}$C-F1 induced mucosal antibody to the F1-antigen whereas bacteria expressing the F1-antigen expressed from the lacZ or ompC promoters failed to induce mucosal responses. Therefore, the measurement of the colonisation of spleen or liver tissues, as an indicator of vaccine potential of recombinant *Salmonella*, may not always be useful.

Similar conclusions were reached by Covone et al. (Covone M G, et al., Infect. Immun. 1998;66:224-31) who showed that effective delivery of the LTK63 guest antigen to the immune system was effective only when the antigen was delivered during the early stages of invasion and by McSorley et al. (McSorley S J, et al., Infect. Immun. 1997;65:171-78) who showed that recombinant *Salmonella* expressing glycoprotein 63 from the osmC promoter were unable to invade tissue beyond the mediastinal lymph nodes, yet induced protection against *Leishmania major*. This might also explain why killed *Salmonella* with or without guest antigens, which are clearly not able to invade deep host tissues, are able to induce an immune response (Thatte J, et al., Int. Immunol. 1993;5:1431-36).

The ability of *Salmonella* expressing $P_{phoP-F}1$ to induce mucosal antibody responses to the F1-antigen in both the gut and the lungs, whereas a constitutive promoter ($P_{lacZ}$) failed to induce such responses clearly demonstrates the utility of in vivo induced promoters for the induction of appropriate antibody responses. This promoter system will be particularly useful for other applications where a mucosal antibody response is important for protection against disease.

BRIEF DESCRIPTION OF THE DRAWINGS

The invention will now be particularly described by way of Example with reference to the accompanying diagrammatic drawings in which:

FIG. 6 shows sequences of promoters used in the evaluation of the invention.

EXAMPLE 1

Preparation of Bacterial Strains, Cultivation and Enzymes

*Escherichia coli* strain JM109 and *S. typhimurium* strains LB5010 (rm*galE), SL3261 (aroA) or SL1344 (a mouse-virulent strain; (Zhang X, et al., Infect. Immun. 1997;65: 5381-7) were cultured on L-agar or in L-broth, supplemented with ampicillin (05 μg/ml) where appropriate. Enzymes used for DNA cloning and amplification procedures were obtained from BCL limited (Lewes, Sussex, UK). PCR reactions were carried out using a Perkin Elmer 9600 (P.E. Applied Biosystems, Warrington, UK) thermal cycler with cycle conditions of 95° C., 5 min, followed by 50 cycles of 95° C., 5 s; 45° C., 5 s; 72° C., 5 s, followed by 10 min at 72° C.

Plasmids containing promoters for expression of F1-antigen were then produced. The promoters for the phoP, pagC and ompC genes have previously been mapped and upstream regulatory regions identified (Soncini F C, et al., J. Bacteriol. 1995;177:4364-71, Pulkkinen W S, et al., J. Bacteriol. 1991; 173:86-9, Puente J L, et al., Gene. 1987;61:75-83, Puente J L, et al., Gene. 1989;83:197-206). For the phoP gene promoter a 139 bp DNA fragment was identified which included the phoPp1 and phoPp2 gene promoters and 80 cp upstream of the −35 site which has been predicted to form step loop structures (Soncini F C, et al., J. Bacteriol. 1995;177:4364-71). For the pagC gene promote a 715 bp DNA fragment included 125 bp upstream of the −35 region (Pulkkinen W S, et al., J. Bacteriol. 1991;173:86-9). For the ompC gene promoter a 371 bp DNA fragment included a 275 bp region upstream of the −35 region (Puente J L, et al., Gene. 1987; 61:75-83, Puente J L, et al., Gene. 1989;83:197-206).

These DNA fragments were amplified from *S. typhimurium* strain SL1344 genomic DNA using the PCR. For comparison with a constitutive gene promoter, a 196 bp DNA fragment encoding the lacZ gene promoter and 140 bp upstream of the −35 region was identified. The 3' end of all of the DNA fragments terminated before the SD regions associated with the genes. These promoters were cloned upstream of the caf1 open reading frame (encoding the *Y. pestis* F1-antigen) and SD region in a low copy number vector (pBR322; FIG. 1) and the recombinant plasmids ($pP_{ompC}$-F1, $pP_{phop}$-F1, $pP_{pagC}$-F1 or $pP_{lacz}$-F1) transformed into *S. typhimurium* SL3261 (aroA).

Oligonucleotide primers were designed to amplify promoter regions using the PCR (Table 1).

TABLE 1

| Oligonucleotide pair | SEQ ID No | Prom |
|---|---|---|
| 5' AAGGAAAAAAGCGGCCGCCGCCCAATACGCAAACCG 3' | 5 | |
| 5' GAATTCACTAGTATTGTTATCCGCGCTCACAAT 3' | 6 | Plac |
| 5' AAGGAAAAAAGCGGCCGCTGACTCTGGTCGACGAACTTA 3' | 7 | |
| 5' CTAGTCTAGATGTGTTAACCAATAAGAACAGTCTA 3' | 8 | PphoP |
| 5' AAGGAAAAAAGCGGCCGCTAAACAGACATTCAGAAGTGAATG3' | 9 | |
| 5' CTAGTCTAGAATATGCCTTTATTGCTTTTTTATG 3' | 10 | PompC |
| 5' AAGGAAAAAAGCGGCCGCGTTAACCACTCTTAATAATAATG 3' | 11 | |
| 5' CTAGACTAGTTACTACTTATTATTTACG 3' | 12 | PpagC |

Restriction sites are shown underlined.

The primers included unique Not1, Xbal or Spel sites. Regions amplified included the −10 and −35 regions and upstream regulatory binding sites, but excluded the Shine-Dalgarno (SD) ribosome binding site.

After PCR amplification of the promoter regions from *S. typhimurium* SL 1344 template DNA (or plasmid pUC18 template DNA for amplification of the lac promoter), the DNA fragments were purified using Microcon 100 centrifugal concentrations (Millipore, Watford, UK). The purified DNA fragments were cloned into suitable digested plasmid pBluescript, SK-, electroporated into *E. coli* JM101 and the cloned fragments were nucleotide sequenced to ensure their authenticity. After digestion of the recombinant plasmids with SacI and BssHII and agarose gel electrophoresis, DNA fragments containing the promoter regions were purified using Qiaex (Qiagen Ltd, Crawley, UK) and blunt ended using Klenow fragment (Sambrook J, Frtisch E F, Maniatis T. 1989. Molecular Cloning: A Laboratory Manual, 2nd ed. Cold Spring Harbor Laboratory press, New York).

The authentic promoter sequences were then cloned into plasmid pBR322 which had been digested with EcoRl and Nrul and then blunt ended using Klenow fragment (Sambrook J, Frtisch E F, Maniatis T. 1989. Molecular Cloning: A Laboratory Manual, 2$^{nd}$ ed. Cold Spring Harbor Laboratory press, New York). The orientation of the cloned DNA fragment in the plasmid was determined by analysing, using agarose gel electrophoresis, the DNA fragments obtained after digestion with Xbal, Sspl or Styl.

A DNA fragment which encoded the Caf1 open reading frame and the ribosome binding site was isolated after digestion of plasmid pORF1 (Oyston P C F, et al., Infect. Immun. 1995;63:563-68) with EcoRl followed by blunt ending of the DNA and further digestion with Hindlll. The purified DNA fragment was ligated with promoter plasmids with which had been digested with Smal and Hindlll. The final recombinant plasmids were transformed into *E. coli* strain JM109.

Plasmids were isolated from *E. coli* (Sambrook J, Frtisch E F, Maniatis T. 1989. Molecular Cloning: A Laboratory Manual, 2$^{nd}$ ed. Cold Spring Harbor Laboratory press, New York) and electroporated into *S. typhimurium* SL3281 (aroA) after passage through *S. typhimurium* LB5010 to ensure methylation of the DNA.

EXAMPLE 2

The stability of the different plasmids encoding F1-antigen driven from different promoters in *S. typhimurium* SL3261 was determined after culture of the bacteria in L-broth for 24 hr (in vitro stability) and enumeration of bacteria which grew on L-agar or L-agar containing amplicillin (Sambrook J, Frtisch E F, Maniatis T. 1989. Molecular Cloning: A Laboratory Manual, $2^{nd}$ ed. Cold Spring Harbor Laboratory press, New York). The results indicated that all of the plasmids were retained by at least 80% of the bacteria which had been cultured in vitro (p$P_{ompC}$-F1, 83%; p$P_{phoP}$-F1, 100%; p$P_{pagC}$-F1, 98%; p$P_{lacZ}$-F1, 95%).

EXAMPLE 3

Colonisation of Host Tissues

The in vivo stability of plasmids was determined by inoculating groups of 10 female BALB/c mice orally with $10^9$ cfu of bacteria in 100 μl of PBS, and enumerating bacteria isolated 11 days later from homogenised spleen tissue on L-agar or L-agar+ampicillin.

In the case of the $P_{pagC}$-F1 construct and the *S. typhimurium* SL3261 control strain, bacteria were also cultured from mesenteric lymph nodes (10/mouse) each homogenised in 2 ml of PBS or from homogenised liver tissue which were removed on 11 days after dosing. Bacteria were enumerated bacteria as described above.

With the exception of the bacteria containing the $P_{pagC}$-F1 plasmid and the SL3261 control bacteria, ampicillin-resistant bacteria could be recovered from all of the spleens isolated from orally dosed mice. The in vivo stability of all of the plasmids within *Salmonella* was lower than the stability of the plasmids within *Salmonella* cultured in vitro.

Although mice were dosed orally with similar numbers of bacteria there were marked differences in the level of colonisation of spleen tissues at day 11 (FIG. 2). The highest levels of colonisation were found with bacteria containing p$P_{phoP}$-F1. Low numbers of *Salmonella* containing p$P_{pagC}$-F1 were recovered from spleen tissues (maximum 50 cfu/spleen) and none of the bacterial colonies were amplicillin resistant. To investigate why the presence of the p$P_{pagC}$-F1 affected the colonising ability of this *Salmonella,* a more detailed study was undertaken which involved the enumeration of bacteria in the liver and in mesenteric lymph nodes 11 days after oral dosing. The levels of SL3261 containing p$P_{pagC}$-F1 isolated from liver tissues were similar to those isolated from spleens (data not shown). Whereas the mean number of SL3261 isolated from mesenteric lymph nodes was $2.2\times10^3$ cfu, SL3261 containing p$P_{pagC}$-F1 could be isolated only at low level (mean 20 cfu) from these tissues.

EXAMPLE 4

Serum Antibody Responses to F1-antigen

Groups of 5 or 8 female BALB/c mice were immunised via intragastric intubation on days 0 and 14 with $1\times10^9$ cells of the $P_{ompC}$-F1, $P_{phoP}$-F1, $P_{pagC}$-F1 or $P_{lacZ}$-F1 constructs, or the control *S. typhimurium* strain, SL3261, in 0.1 ml of phosphate-buffered saline (PBS). Bacteria were grown statically overnight at 37° C. All oral inoculations were carried out with a stainless steel gavage needle without an anaesthetic. The inoculum dose was verified by plating serial dilutions of each culture on L-agar plates with or without ampicillin.

On days 21, 28 and 98 mice were anaesthetized by intraperitoneal (i.p.) administration of a cocktail of domitor (6 mg per dose) and Ketalar (27 mg per dose) and blood was collected by cardiac puncture. Mice were then sacrificed by cervical dislocation. Blood was allowed to clot at 4° C. overnight prior to centrifugation (10,000×g, 10 minn, 4° C.) and the serum stored at −20° C. until tested.

After i.g. dosing with the recombinant *Salmonella,* mice in all groups developed IgG serum antibody to the carrier bacterium, which reached a maximum level 98 days after immunisation (FIG. 3*a*). In the case of SL3261 expressing $P_{pncP}$-F1, the onset of the immune response was delayed. All groups of mice developed IgG serum antibody to F1-antigen (FIG. 3*b*), which had reached a peak at day 28 and declined by day 98. There was no significant difference in the peak titres to F1-antigen induced by the different recombinant *Salmonella.*

When the isotype of this antibody was determined on day 98, it was found to be predominantly of an $IgG2_a$ isotope in all groups of immunised animals (FIG. 4), suggesting that a Th1-type response was induced. Several other workers have shown that recombinant *S. typhimurium* induce a Th1-type response to the guest antigen (Brett S J, et al., Immunology 1993;80:306-12, Thatte J, et al., Int. Immunol. 1993;5:1431-36).

EXAMPLE 5

Mucosal Antibody Responses to F1-antigen

The ability of the different recombinant *Salmonella* to induce a mucosal antibody response after i.g. dosing was determined by measuring the levels of circulating IgA antibody to F1-antigen or the levels of IgA antibody to F1-antigen in gut or lung wash samples. After dosing as described in Example 4, on days 21 and 28, gut and lung wash samples were collected. Briefly, gut wash samples were collected by resecting a 10 cm length of small intestine and flushing with 5 ml of PBS. Samples were sonicated for 0.5 min prior to centrifugation (12,000×g, 30 mins 4° C.) and the supernatant was decanted and lyophilized. Broncho-alveolar washings were collected from individual animals by injecting 5 ml of chilled lavage medium (0.9% (w/v) NaCl, 0.05% (v/v) tween 20, 0.1% (w/v) $NaN_3$ and 1 mM phenylmethylsulfonyl fluoride) into the trachea using an intravenous canula and inflating the lungs. A syringe was used to remove the washings, which were subsequently centrifuged (12,000×g, 30 min, 4° C.) prior to lyophilisation of the supernatant fluid. Gut and lung wash samples were reconstituted in 200 μl sterile water immediately before use.

All measurements of antibody levels in individual animals were determined in duplicate. For enzyme-linked immunosorbent assays (ELISAs) to determine IgG and IgA titres, 96-well microtiter plates were coated overnight at 4° C. either with 50 µl 5 µg/ml purified F1-antigen (Miller J, et al., FEMS Microbiology and Immunology 1998;21:213-21) in PBS or with 50 µl 6 µg/ml S. typhimurium SL3261 lysate in PBS, prepared as follows. Bacteria were grown statically overnight at 37° C., prior to harvesting and resuspension in PBS to an approximate concentration of $1\times10^{10}$ cfu/ml. Cells were heat-killed in a boiling water bath for 30 minutes, cooled on ice and then sonicated on ice for 6 pulses of 30 seconds. Total protein concentration was determined by a BCA protein assay (Pierce and Warriner, Chester, UK). Plates were blocked for 1 hour at 37° C. with PBS containing 1% (w/v) skimmed milk powder (BLOTTO). Serum, gut and lung wash samples were diluted in BLOTTO, and 50 µl volumes were assayed in duplicate in a series of twofold dilutions. After incubation overnight at 4° C., plates were washed three times in PBS with 0.02% (v/v) TWEEN 20™ (Polysorbate 20). Peroxidase-conjugated secondary antibodies against mouse IgG or IgA (Harlan Sera-Lab Ltd, Loughborough, UK), diluted 1:2000 in BLOTTO were incubated for 1 hour at 37° C. The plate was washed as previously and 100 µl of 2,2'-azino bis(3-ethybenzthiazoline-6-sulfonic acid) substrate (ABTS; Sigma, Poole, UK) was added. Antibody titre was estimated as the maximum dilution of serum giving an absorbance $_{414nm}$ reading 0.1 U above background (Sera from animals immunized with SL3261 alone).

To determine $IgG_1$, or $IgG_{2a}$ concentrations, ELISAs were performed essentially as above, except that wells were coated with 10 µg/ml anti-mouse IgG (Fab-specific, Sigma, Poole, UK) 5 µg/ml purified F1-antigen in PBS or 6 µg/ml S. typhimurium SL3261 lysate. Purified $IgG_1$ or $IgG_{2a}$ (Sigma, Poole, UK) and day 98 serum samples were diluted in BLOTTO. Peroxidase-labelled secondary antibodies against mouse $IgG_1$ or $IgG_{2a}$ were diluted 1:4000 BLOTTO before use.

Figure 1:
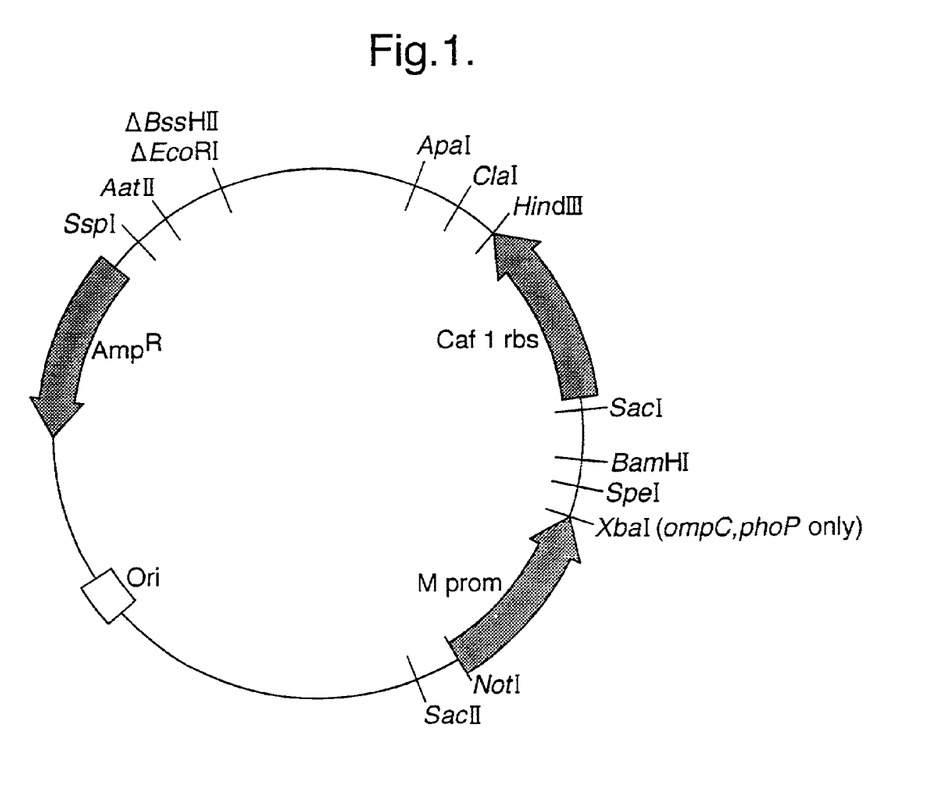
FIG. 1 is a plasmid diagram illustrating plasmids used in the preparation of microorganisms in accordance with the invention.
Figure 2:
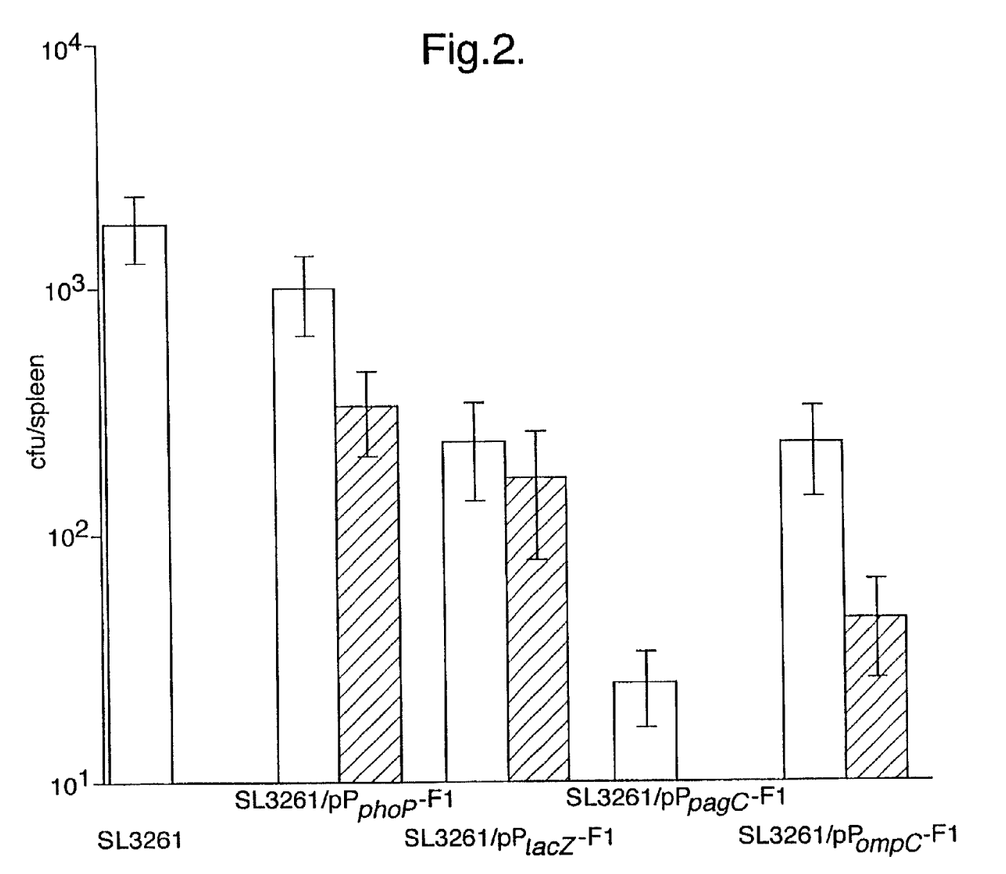
FIG. 2 is a graph showing the levels of colonisation of spleen tissues of mice, 11 days after dosing with recombinant microorganisms of the invention.
Figure 3A:
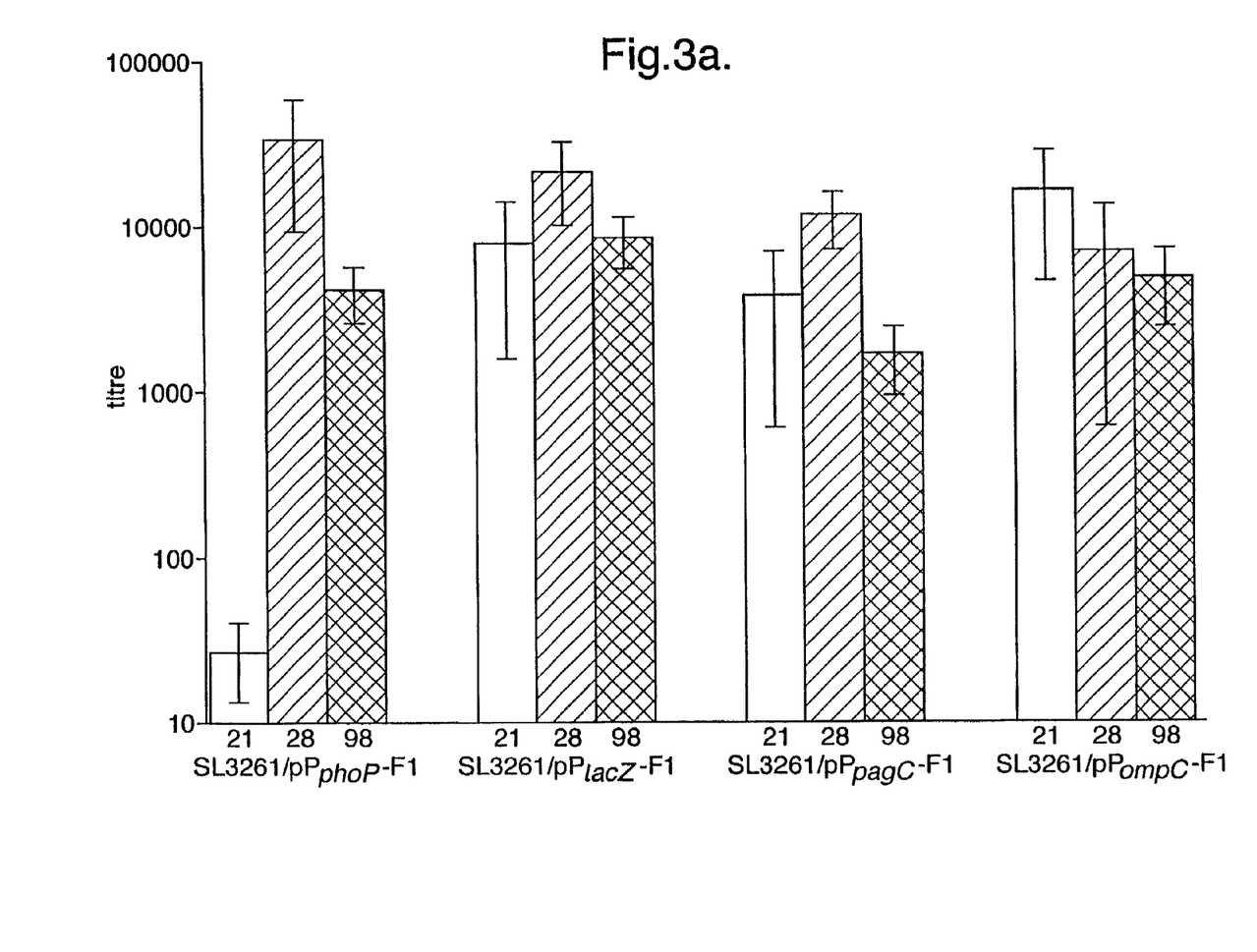
FIGS. 3a and 3b show graphs illustrating IgG serum antibody levels in mice to the carrier bacterium, (FIG. 3a) and to the F1 antigen (FIG. 3b), 21, 28 and 98 days after immunization.
Figure 3B:
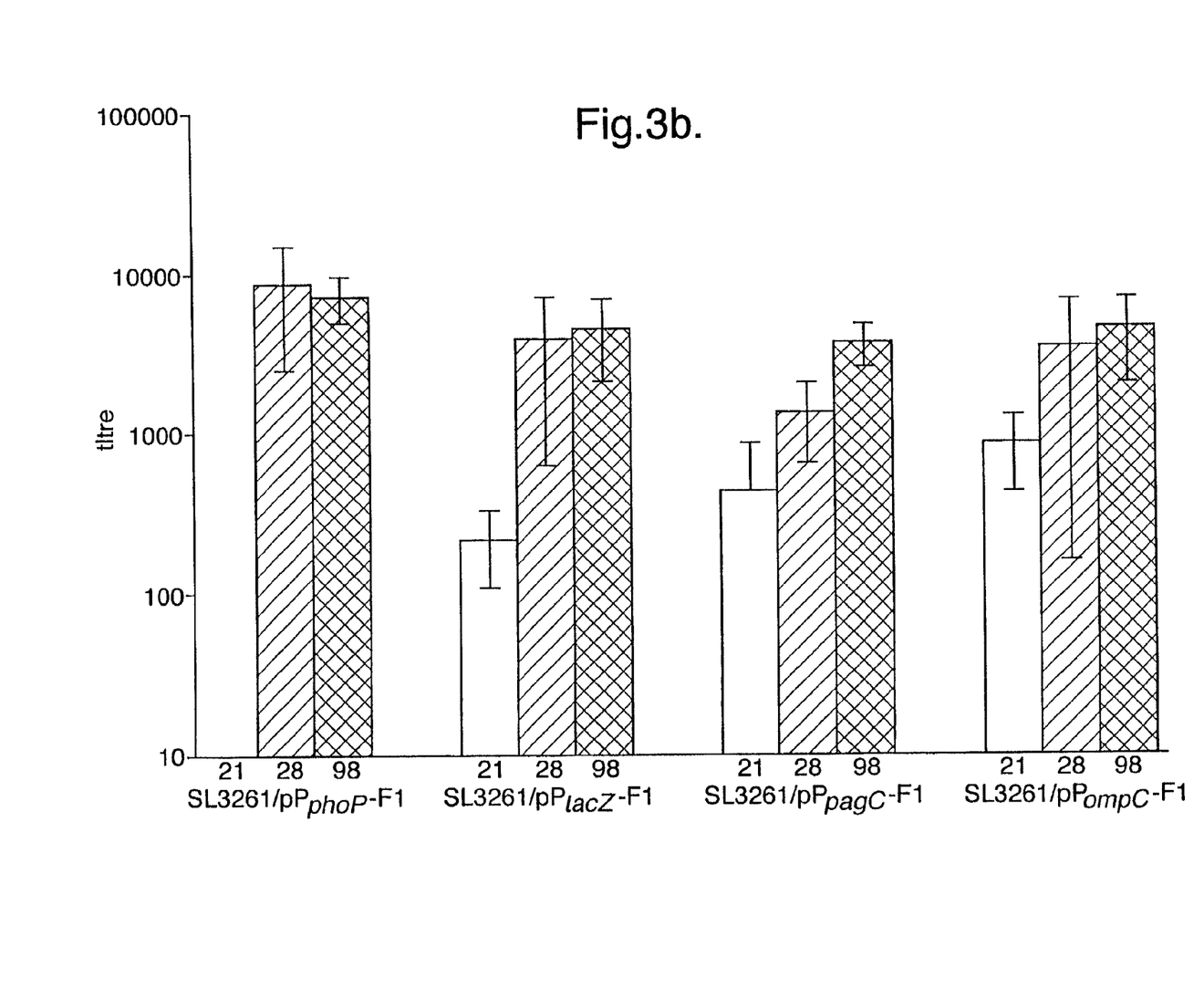
Figure 4:
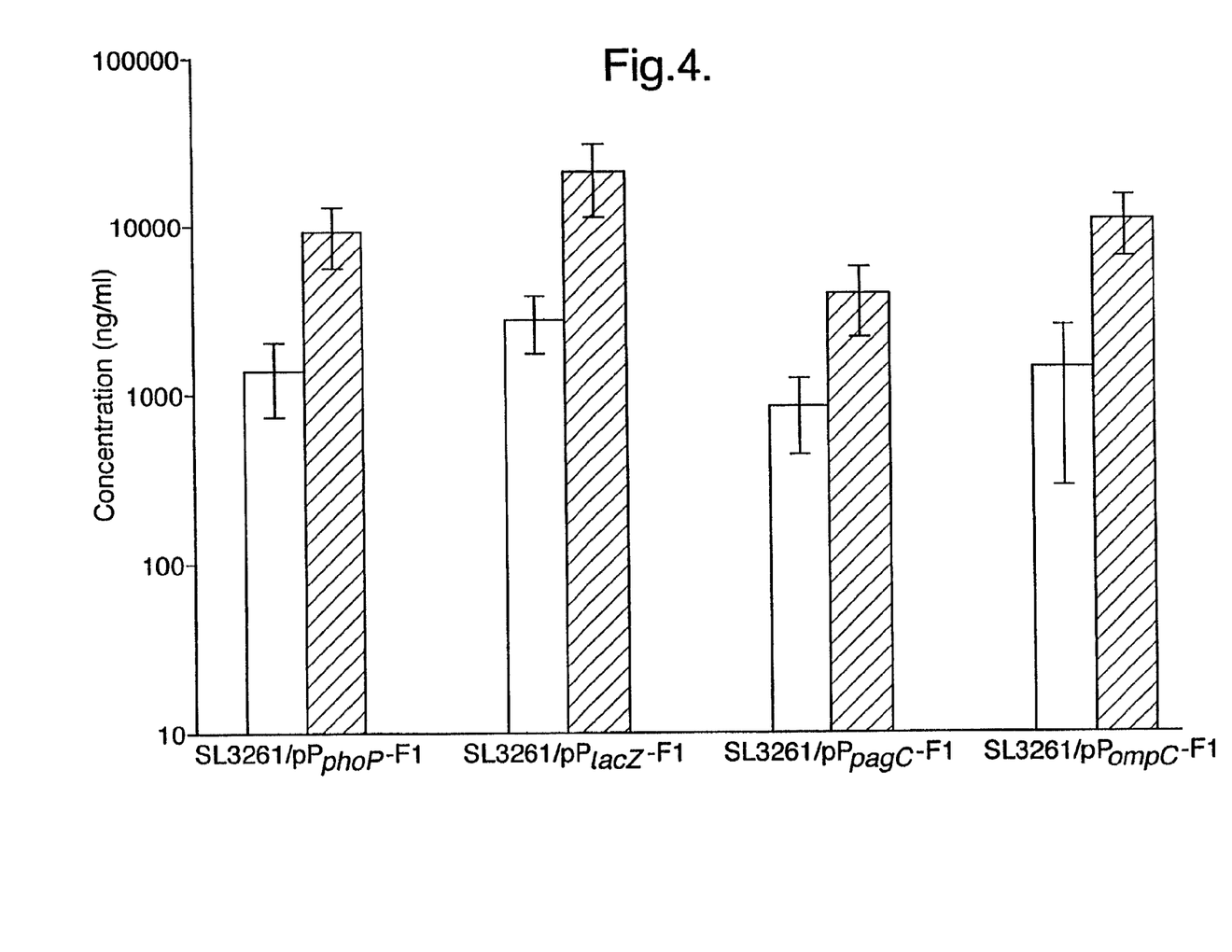
FIG. 4 is a graph showing the isotype of the F1 antibody found in mice serum on day 98, where the blank column represents the amount of the $IgG1_a$? and the shaded column represents the $IgG2_a$ isotype in all groups of immunised animals.
Figure 5:
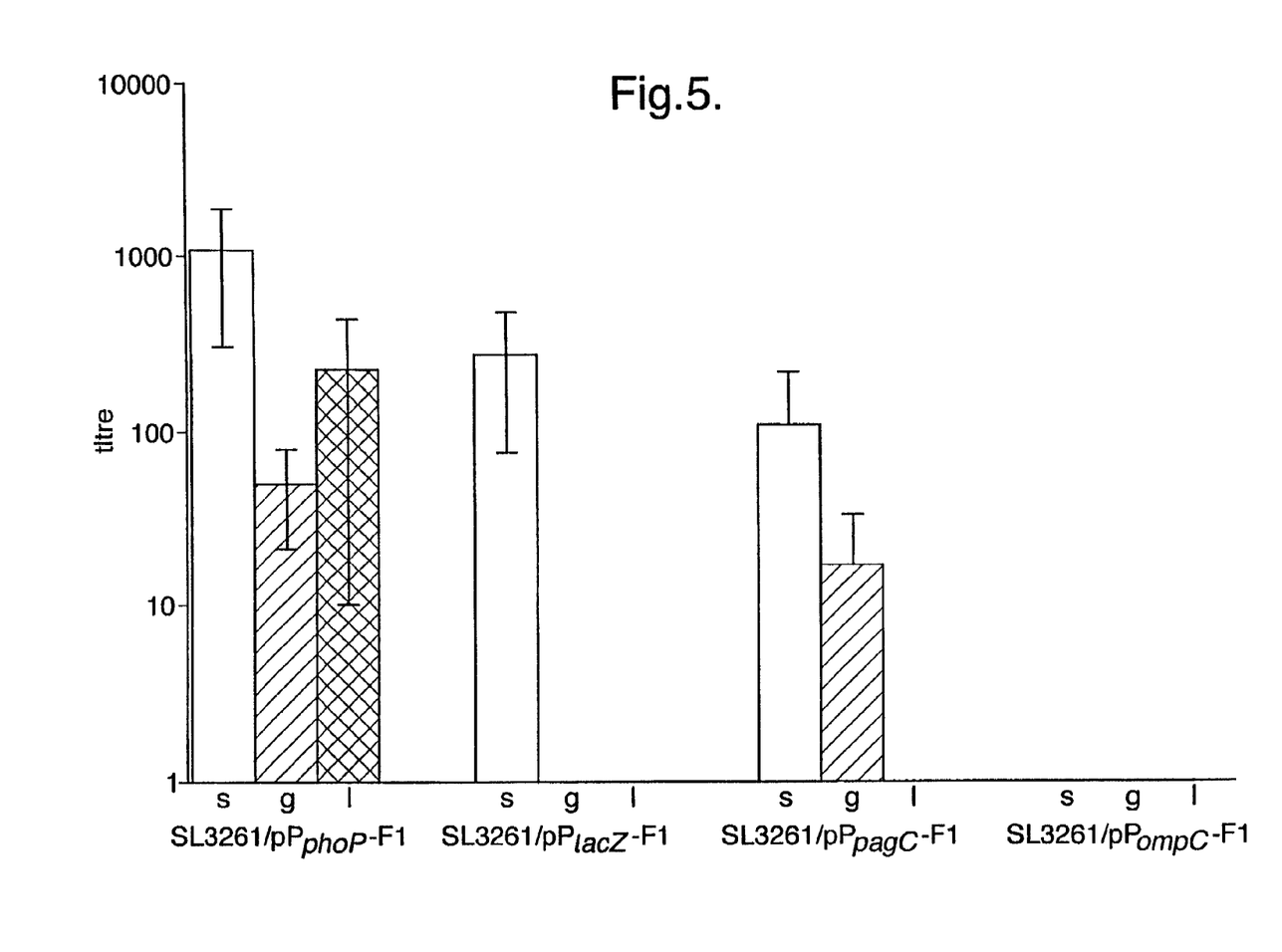
FIG. 5 is a graph showing the levels of circulating IgA antibody to F1-antigen or the levels of IgA antibody to F1-antigen in gut (blank column) or lung (shaded column) wash samples.

The results (FIG. 5) indicated that SL3261 containing $pP_{pncP}$-F1, $pP_{lacZ}$-F1 or $pP_{pagC}$-F1 plasmids all induced serum IgA antibody to F-antigen. The induction of circulating IgA to F1-antigen did not correlate with the presence of IgA to F1-antigen at mucosal surfaces. For example, SL3261/$pP_{lacZ}$-F1 induced high levels of serum antibody to F1-antigen but IgA antibody to F1-antigen was not detected in gut or lung wash samples. Only SL3261/$pP_{phoP}$-F1 induced an IgA antibody response to F1-antigen in both the gut and the lung.

EXAMPLE 6

Production of IgA by Peyer's Patch Cells

Peyer's patches were also removed to determine the presence of F1- and Salmonella specific IgA producing cells in the gut. Briefly, a total of 8 Peyer's patches were removed from 5 mice in each treatment group (see Example 4) and pooled. Cells were separated by crushing through a cell strainer, washed by centrifugation and resuspended in 1.4 ml of Dulbeccos Modified Eagles Medium (DMEM)+10% foetal calf serum (FCS). Duplicate samples (100 µl/well) were then plated onto plates previously coated with 5 µl/ml F1 or 6 µg/ml S. typhimurium SL3261 lysate and blocked with 20% FCS in DMEM, and incubated for 48 hours at 37° C. Plates were washed and incubated for 1 hour with peroxidase-labelled secondary antibody against mouse IgA, diluted 1:2000 in PBS before use, and developed with 100 µl of ABTS.

Figure 7A:
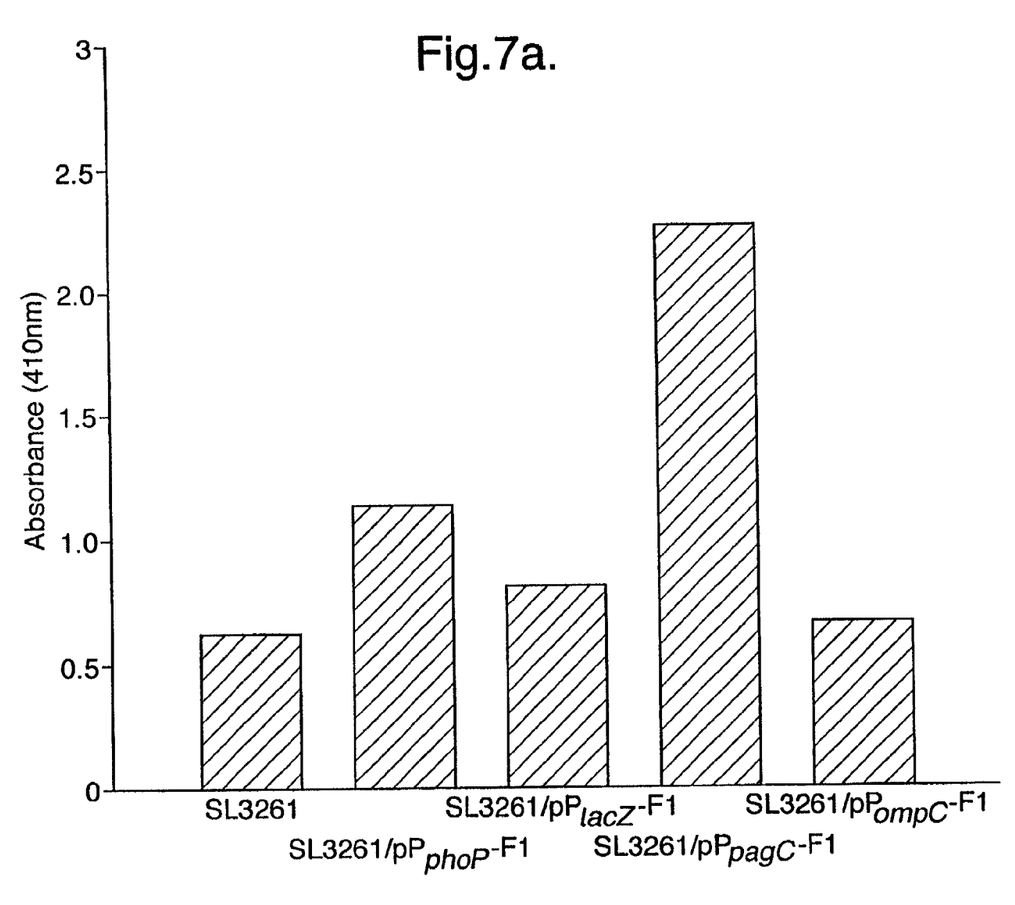
FIGS. 7a and 7b show the results of elispot analysis of Peyer's patch cells and in particular the IgA response against F1 antigen (FIG. 7a) and *Salmonella* (FIG. 7b).

The results are shown in FIG. 7. These show showed that the secretion of IgA against F1-antigen was greatest in Peyer's patch cells isolated from mice which had been immunised with SL3261 containing $pP_{pagC}$-F1 (FIG. 7a). Peyer's patch cells taken from mice which had been immunised with SL3261/$pP_{phoP}$-F1 also produced IgA. Cells taken from other groups produced only low levels of IgA to F1-antigen.

Figure 7B:
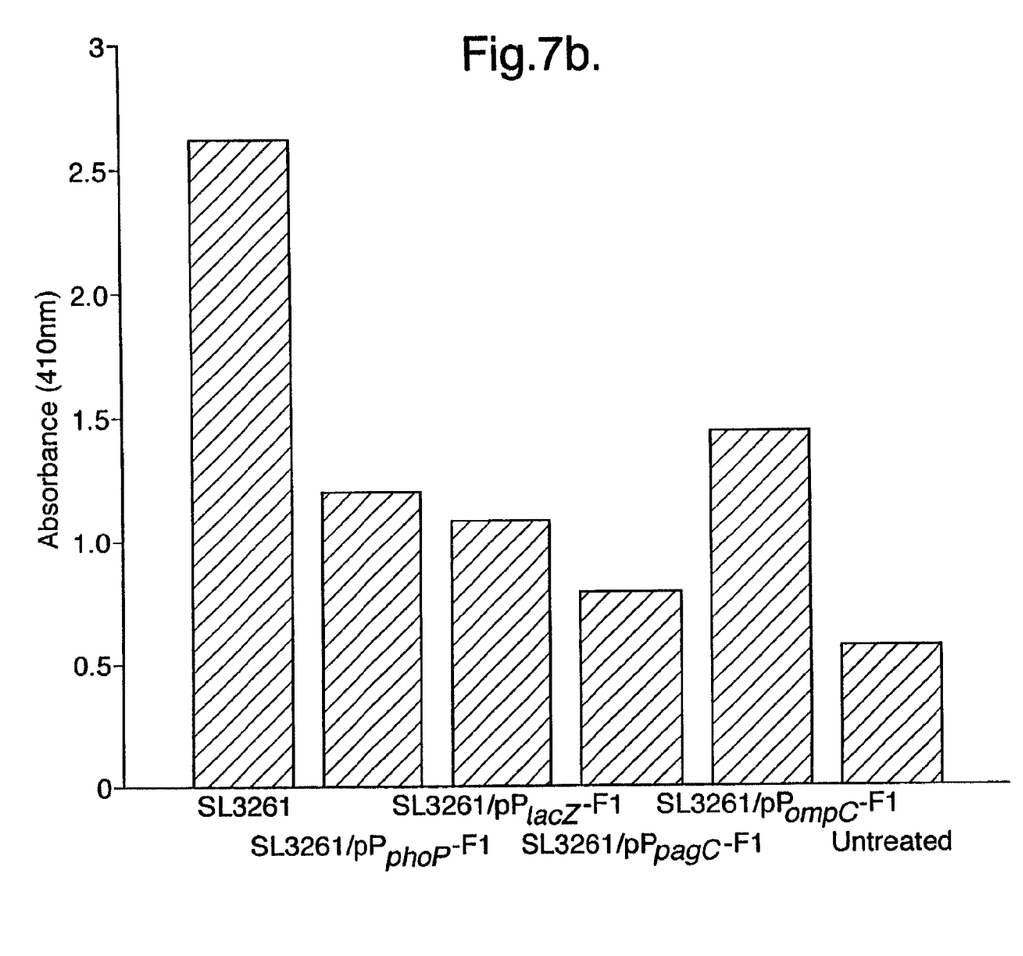

This pattern of response was not reflected in the pattern of production of IgA against Salmonella; Peyer's patch cells taken from mice which had been immunised with SL3261/$pP_{pagC}$-F1 produced only low levels of antibody to Salmonella (FIG. 7b).

The invention claimed is:

1. A method of causing expression of a desired heterologous protein in gsstrointestinal mucosal cells of a mammal, the method comprising placing a nucleotide sequence encoding the desired heterologous protein under the control of a promoter consisting of the nucleotide sequence of SEQ ID NO: 2, the promoter being operatively interconnected to the nucleotide sequence encoding the desired heterologous protein, in a recombinant gut-colonizing bacterium, wherein the recombinant gut-colonizing bacterium is suitably attenuated so that the mammal does not experience significant harmful effects as a result of infection by the recombinant gut-colonizing bacterium, orally administering the recombinant gut-colonizing bacterium to the mammal, and causing the expression of the desired heterologous protein in the gastrointestinal mucosal cells of the mammal.

2. The method of claim 1, wherein the desired heterologous protein induces a protective immune response against a pathogen in the mammal.

3. The method of claim 1, wherein the recombinant gut-colonizing bacterium is a *Salmonella* spp.

4. The method of claim 3, wherein the *Salmonella* spp. is *Salmonella typhimurium* or *Salmonella typhi*.

5. The method of claim 2, wherein the pathogen is *Yersinia pestis*.

6. The method of claim 5, wherein the desired heterologous protein comprises the F1-antigen of *Yersinia pestis*.

7. The method of claim 2, wherein the recombinant gut-colonizing bacterium is administered with a pharmaceutically acceptable carrier or diluent.

8. A method of inducing a serum or mucosal antibody response in a mammal against *Yersinia pestis* comprising expressing F1-antigen of *Yersinia pestis* in an attenuated recombinant *Salmonella* spp. by placing a nucleotide sequence encoding the F1-antigen under control of a promoter consisting of the nucleotide sequence of SEQ ID NO: 2, the promoter being operatively interconnected to the nucleotide sequence, and administering a dosage of the attenuated recombinant *Salmonella* spp. orally to the mammal.

9. The method of claim 8 wherein the *Salmonella* spp. is *Salmonella typhimurium* or *Salmonella typhi*.

10. The method of claim 8 wherein the attenuated recombinant *Salmonella* spp. is administered with a pharmaceutically acceptable carrier or diluent.

* * * * *

SEQUENCE LISTING

<160> NUMBER OF SEQ ID NOS: 12

<210> SEQ ID NO 1
<211> LENGTH: 196
<212> TYPE: DNA
<213> ORGANISM: Salmonella typhimurium

<400> SEQUENCE: 1

```
cgcccaatac gcaaaccgcc tctccccgcg cgttggccga ttcattaatg cagctggcac      60
gacaggtttc ccgactggaa agcgggcagt gagcgcaacg caattaatgt gagttagctc     120
actcattagg cacccaggc tttacacttt atgcttccgg ctcgtatgtt gtgtggaatt     180
gtgagcggat aacaat                                                     196
```

<210> SEQ ID NO 2
<211> LENGTH: 139
<212> TYPE: DNA
<213> ORGANISM: Salmonella typhimurium

<400> SEQUENCE: 2

```
gtgactctgg tcgacgaact taaataatgc ctgcctcacc ctcttttctt cagaaagagg      60
```

```
gtgactattt gtctggttta ttaactgttt atccccaaag caccataatc aacgctagac    120
tgttcttatt gttaacaca                                                139

<210> SEQ ID NO 3
<211> LENGTH: 715
<212> TYPE: DNA
<213> ORGANISM: Salmonella typhimurium

<400> SEQUENCE: 3
gttaaccact cttaataata atgggtttta tagcgaaata gacttttta tcgcgtgttc     60 aatatttgcg ttagttatta ttttttttgga atgtaaattc tctctaaaca caggtgatat  120
ttatgttgga attgtggtgt tgattctatt cttataatat aacaagaaat gttgtaactg  180
atagatatat taaaagatta atcggagcg ggaataaagc gtgctaagca tcatcgtgaa   240
tatgattaca gcgcctgcga tggcatataa ccgtattgcg gatggagcgt cacgtgagga  300
ctgtgaagca caatgcgata tgttctgatt atatggcgag tttgcttaat gacatgtttt  360
tagccgaacg gtgtcaagtt tcttaatgtg gttgtgagat tttctcttta aatatcaaaa  420
tgttgcatgg gtgatttgtt gttctatagt ggctaaacac tttatggttt ctgttaaata  480
tatatgcgtg agaaaaatta gcattcaaat ctataaaagt tagatgacat tgtagaaccg  540
gttacctaaa tgagcgatag agtgcttcgg tagtaaaaat atctttcagg aagtaaacac  600
atcaggagcg atagcggtga attattcgtg gttttgtcga ttcggcatag tggcgataac  660
tgaatgccgg atcggtactg caggtgttta acacaccgt aaataataag tagta        715

<210> SEQ ID NO 4
<211> LENGTH: 371
<212> TYPE: DNA
<213> ORGANISM: Salmonella typhimurium

<400> SEQUENCE: 4
taaacagaca ttcagaagtg aatgacggta ataataaag ttaatgatga tagcggtcac     60
tattttagtt gcgaatgaag attctgtttt atcattcagt gctatgaatt tcatcaattt   120
aacccgttga ttttaaaagt ttcgtgaaat atattttgtc tatttgtgct tattttttact 180 tgattttgc tttaaaaaag ttccgtaaaa ttcatatttt gaaacatcta tatagataac   240
tgtaacatct aaaagttttt agtatcatat tcgtgttgga ttattctgta tttttgcgga  300
gaatggactt gccgactggt taatgagggt taaccagtaa gcagtggcat aaaaaagcaa  360
taaaggcata t                                                       371

<210> SEQ ID NO 5
<211> LENGTH: 36
<212> TYPE: DNA
<213> ORGANISM: Escherica coli

<400> SEQUENCE: 5
aaggaaaaaa gcggccgccg cccaatacgc aaaccg                             36

<210> SEQ ID NO 6
<211> LENGTH: 33
<212> TYPE: DNA
<213> ORGANISM: Escherica coli

<400> SEQUENCE: 6
gaattcacta gtattgttat ccgcgctcac aat                                33
```

-continued

```
<210> SEQ ID NO 7
<211> LENGTH: 39
<212> TYPE: DNA
<213> ORGANISM: Salmonella typhimurium

<400> SEQUENCE: 7
aaggaaaaaa gcggccgctg actctggtcg acgaactta                              39

<210> SEQ ID NO 8
<211> LENGTH: 35
<212> TYPE: DNA
<213> ORGANISM: Salmonella typhimurium

<400> SEQUENCE: 8
ctagtctaga tgtgttaacc aataagaaca gtcta                                  35

<210> SEQ ID NO 9
<211> LENGTH: 42
<212> TYPE: DNA
<213> ORGANISM: Salmonella typhimurium

<400> SEQUENCE: 9
aaggaaaaaa gcggccgcta aacagacatt cagaagtgaa tg                          42

<210> SEQ ID NO 10
<211> LENGTH: 34
<212> TYPE: DNA
<213> ORGANISM: Salmonella typhimurium

<400> SEQUENCE: 10
ctagtctaga atatgccttt attgcttttt tatg                                   34

<210> SEQ ID NO 11
<211> LENGTH: 41
<212> TYPE: DNA
<213> ORGANISM: Salmonella typhimurium

<400> SEQUENCE: 11
aaggaaaaaa gcggccgcgt taaccactct taataataat g                           41

<210> SEQ ID NO 12
<211> LENGTH: 28
<212> TYPE: DNA
<213> ORGANISM: Salmonella typhimurium

<400> SEQUENCE: 12
ctagactagt tactacttat tatttacg                                          28
```